United States Patent [19]

Hall et al.

[11] 4,172,147
[45] Oct. 23, 1979

[54] 3,5-DINITRO OXANILIC ACID ESTER COMPOUNDS, COMPOSITIONS AND METHODS

[75] Inventors: Charles M. Hall; John B. Wright, both of Kalamazoo, Mich.

[73] Assignee: The Upjohn Company, Kalamazoo, Mich.

[21] Appl. No.: 742,439

[22] Filed: Nov. 17, 1976

[51] Int. Cl.² ........................ C07C 79/46; A01N 9/20
[52] U.S. Cl. .................................. 424/309; 560/20; 560/23
[58] Field of Search ............... 260/471 A; 424/309; 560/20, 23

[56] References Cited

U.S. PATENT DOCUMENTS

| 3,317,584 | 5/1967 | Stoffee et al. | 260/465 |
| 3,966,965 | 6/1976 | Sellstedt et al. | 424/309 |

FOREIGN PATENT DOCUMENTS

| 2525226 | 12/1975 | Fed. Rep. of Germany . |
| 2273523 | 2/1976 | France . |

OTHER PUBLICATIONS

Tiere, Rec. Trav. Chem., 52, 420 (1933).
Baker et al., J. Org. Chem. 27, 3283 (1962), p. 3288.
Edmond et al., Brit. J. Pharmacol. Chemother. 27, 415 (1966).
Baker, J. Theoret. Biol., 3, 446, (1962), Table 2, p. 450.

*Primary Examiner*—Donald G. Daus
*Assistant Examiner*—Lisa Jones
*Attorney, Agent, or Firm*—Martin B. Barancik

[57] ABSTRACT

Novel compounds of the formula

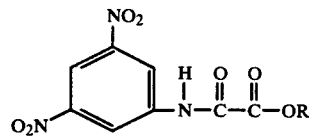

wherein R is alkyl of one to eight carbon atoms, inclusive, are formulated into pharmaceutical compositions suitable for oral or parenteral administration which are used as agents to prophylactically inhibit the allergic manifestations of a sensitized mammal.

25 Claims, No Drawings

3,5-DINITRO OXANILIC ACID ESTER COMPOUNDS, COMPOSITIONS AND METHODS

BRIEF SUMMARY OF THE INVENTION

It has now been discovered that novel compounds of Formula 1 are useful in the prophylactic treatment of sensitized humans and animals for allergy and anaphylactoid reactions of a reagin or non-reagin mediated nature. The compounds are formulated with pharmaceutical carriers for oral or parenteral means of administration.

DETAILED DESCRIPTION OF THE INVENTION

In accordance with this invention, there are provided compounds represented by Formula 1

$$\underset{O_2N}{\overset{NO_2}{\underset{}{\bigcirc}}}-\underset{H}{N}-\underset{\overset{\|}{O}}{C}-\underset{\overset{\|}{O}}{C}-OR \quad \text{Formula 1}$$

wherein R is alkyl of one to eight carbon atoms, inclusive.

It is preferred for R to have two or four carbon atoms, inclusive.

Ethyl 3',5'-dinitro-oxanilate is the preferred compound.

The phrase "alkyl of one to eight carbon atoms, inclusive" is intended to cover methyl, ethyl, propyl, butyl, pentyl, hexyl, heptyl, octyl, and isomers thereof. Illustrative examples of isomers are isopropyl, tert. butyl, neopentyl, 2,3-dimethylbutyl, 2-methylhexyl and 2,2,4-trimethylpentyl.

The compounds are readily prepared by reacting 3',5'-dinitroaniline with an alkyl oxalyl halide, preferably chloride, alkyl being one to eight carbon atoms, inclusive, preferably two or four carbon atoms, inclusive. The reaction is carried out in a suitable solvent and base to form the oxamate.

Examples of suitable solvents are dimethylformamide, dioxane, and tetrahydrofuran. Appropriate bases include triethylamine, N-methylmorpholine, dimethylpiperazine, and N-methylpiperidine.

An alternative method of preparing the oxamate is to react the 3',5'-dinitro aniline with a dialkyl oxalate, alkyl being one to eight carbon atoms, inclusive, preferably diethyl oxalate, in neat solution or with an additional solvent such as a xylene or diphenyl ether, if necessary, at a temperature ranging from about 25° C. to the reflux temperature of the system.

If desired, the ester may be prepared by transesterifying an ethyl or other lower 3',5'-dinitro oxanilate.

The following examples are compounds in accordance with this invention.

EXAMPLE 1

Ethyl 3',5'-dinitro oxanilate

A mixture of 3,5-dinitroaniline (10.0 g., 0.0546 mol), triethylamine (6.0 g., 0.0593 mol), ethyl oxalyl chloride (8.0 g., 0.0586 mol) and anhydrous dimethylformamide is stirred at room temperature for 24 hrs. An additional 6.0 g. (0.0593 mol) of triethylamine and 8.0 g. (0.0586 mol) of ethyl oxalyl chloride are added to the reaction and the stirring continued another 24 hrs. The reaction mixture is poured into water (700 ml.) and stirred one hour. The resulting solid is collected and recrystallized from ethanol to give a white solid (13.5 g., m.p. 120°, 87% yield).

Analysis Calcd. for: $C_{10}H_9N_3O_7$: C, 42.41; H, 3.20; N, 14.84. Found: C, 42.58; H, 3.19; N, 14.74.

EXAMPLE 2

The oxanilate of Example 1 is transesterified to prepare the following 3',5'-dinitro oxanilates:

R
methyl
n-propyl
isopropyl
n-butyl
tert. butyl
n-pentyl
neopentyl
n-hexyl
2,3-dimethylbutyl
n-heptyl
2-methylhexyl
n-octyl
2,2,4-trimethylpentyl The compositions of the present invention are presented for administration to humans and animals in unit dosage forms, such as tablets, capsules, pills, powders, oral solutions or suspensions, and oil-in-water or water-in-oil emulsions containing suitable quantities of the compound of Formula 1. The preferred method of administration is oral.

For oral administration, either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. the water-suspendable forms can be mixed with an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration, can be either suspended or dissolved in the vehicle. In preparing solutions the compound can be dissolved in an oil such as peanut oil and filter sterilized before filling into a suitable vial or ampoule and sealing. Advantageously, adjuvants such as a local anesthetic, preservative and buffering agents can be dissolved or suspended in the vehicle. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The term "unit dosage form", as used in the specification and claims, refers to physically discrete units suitable as unitary dosages for human subjects and animals, each unit containing a predetermined quantity of active material calculated to produce the desired therapeutic diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, powder packets, wafers, granules, cachets, teaspoonfuls, tablespoonfuls, dropperfuls, ampoules, vials, segregated multiples of any of the foregoing and other forms as herein described.

An effective but non-toxic quantity of the compound is employed in treatment. The dosage of the compound for treatment depends on the route of administration and the particular compound. A dosage schedule for humans of from about 0.05 to about 10 mg. in a single dose administered parenterally in the composition of this invention is effective for preventing allergy attacks. More specifically, the single dose is from about 0.5 to about 5 mg. of compound. The oral dose is from about 0.5 to about 30 mg. in a single dose. More specifically the single dose is from about 1 to about 20 mg. of compound. The dosage to be administered can be repeated up to four times daily. However, when it is necessary to repeat treatment, a preferred dosage schedule reduces the secondary treatment dosage to from about 0.5 percent to about 20 percent of the above dosages, more specifically, from about 1 to about 10 percent of the above dosages. In this manner, a state of allergy prophylaxis can be maintained. The reduced dosage is taken until that dosage no longer provides effective protection. At that time, the larger dosage is repeated, followed by the reduced dosage. An example of such a dosage schedule is the following: An asthmatic individual orally administers 10 mg. of ethyl 3',5'-dinitro oxanilate. Four hours later, the individual orally administers 2 mg. of the same compound and every four to six hours thereafter orally administers 2 mg. of the same compound until effective asthma prophylaxis is not provided. The individual then orally administers 10 mg. of the same compound, then reduces the intake to 2 mg. four to six hours later. The dosage schedule continues in this manner.

The administration of the compositions of the present invention to humans and animals provides a method for the prophylactic treatment of allergy or all anaphylactic reactions of a reagin or non-reagin mediated nature. That is to say, these compositions, when administered to a sensitized individual prior to the time that the individual comes into contact with substances (antigens) to which he is allergic, will prevent the allergic reaction which would otherwise occur.

For example, the process can be used for prophylactic treatment of such chronic conditions as bronchial asthma, allergic rhinitis, food allergy, urticaria, and anaphylactoid reactions and exercise and stress induced asthma. Preferred conditions are bronchial asthma, allergic rhinitis, food allergy, urticaria, and anaphylactoid reactions. More preferred conditions are bronchial asthma, allergic rhinitis, and food allergy. Conditions most preferred to be treated with compounds of this invention are bronchial asthma and allergic rhinitis.

EXAMPLE 3

A lot of 10,000 tablets, each containing 30 mg. of ethyl 3',5'-dinitro oxanilate is prepared from the following types and amounts of ingredients:

| | |
|---|---|
| Ethyl 3',5'-dinitro oxanilate | 300 Gm. |
| Dicalcium phosphate | 1,000 Gm. |
| Methylcellulose, U.S.P. (15 cps) | 60 Gm. |
| Talc | 150 Gm. |
| Corn starch | 200 Gm. |
| Magnesium stearate | 10 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever attacks at a dose of one tablet every four to six hours.

EXAMPLE 4

One thousand two-piece hard gelatin capsules, each containing 30 mg. of ethyl 3',5'-dinitro oxanilate are prepared from the following types and amounts of ingredients:

| | |
|---|---|
| Ethyl 3',5'-dinitro oxanilate | 30 Gm. |
| Talc | 150 Gm. |
| Magnesium stearate | 0.75 Gm. |

The ingredients are mixed well and filled into capsules of the proper size.

Capsules so prepared are useful in preventing attacks of bronchial asthma at a dose of one capsule every four to six hours.

EXAMPLE 5

One thousand tablets, each containing 10 mg. of n-butyl 3',5'-dinitro oxanilate are prepared from the following types and amounts of ingredients:

| | |
|---|---|
| n-Butyl 3',5'-dinitro oxanilate | 10 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food allergy at a dose of one tablet every four to six hours.

EXAMPLE 6

One thousand tablets, each containing 20 mg. of n-propyl 3',5'-dinitro oxanilate are prepared from the following types and amounts of ingredients:

| | |
|---|---|
| n-Propyl 3',5'-dinitro oxanilate | 20 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food allergy at a dose of one tablet before meals.

EXAMPLE 7

A sterile preparation suitable for intramuscular injection and containing 5 mg. of ethyl 3',5'-dinitro oxanilate in each milliliter is prepared from the following ingredients:

| | |
|---|---|
| Ethyl 3',5'-dinitro oxanilate | 5 Gm. |
| Benzyl benzoate | 200 ml. |
| Methylparaben | 1.5 Gm. |
| Propyl paraben | 0.5 Gm. |
| Cottonseed oil q.s. | 1,000 ml. |

One milliliter of this sterile preparation is injected for prophylactic treatment of allergic rhinitis.

EXAMPLE 8

In individuals who require continual treatment in the Examples 3-7, the dosage of the Example is given initially and each succeeding administration of the drug is at 1/50 of the initial dosage. This maintenance dosage is continued until effective allergy prophylaxis is not obtained. The initial dosage of Examples 3 through 7 is then started once more, followed by the maintenance dosages.

EXAMPLE 9

After allowing for the different solubilities of the compounds and the activity of the particular compound as measured, for example, by the in vivo rat passive cutaneous anaphylaxis assay, a suitable quantity of each of the compounds of Example 2 is substituted for the active compound in the compositions and uses of Examples 3-7. Results showing anti-allergy activity are obtained.

EXAMPLE 10

The rat passive cutaneous anaphylaxis (PCA) assay is run in the following manner:

Female Sprague-Dawley 250 gm. rats are skin-sensitized with rat anti-ovalbumin homocytotropic anti-body that is heat labile and has a passive cutaneous anaphylaxis titer of 1:128. After a 72-hour latency period, the animals are challenged i.v. with 4 mg. ovalbumin (OA)+5 mg. Evans blue dye and the test compound. The test compound is administered orally in 0.25% methyl cellulose in water at the appropriate time before challenge. Thirty minutes later the extravascular bluing that results from antigen antibody combination at the skin site is read. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots divided by the number of animals.

Compounds of this invention particularly those compounds wherein R is ethyl or n-butyl are quite long acting and potent compounds as shown in the PCA assay. The compound wherein R is ethyl provides 45% inhibition when orally administered at 50 mg./kg. 60 minutes prior to antigen challenge and provides 32% inhibition when orally administered at 1 mg./kg. 20 minutes prior to antigen challenge in the PCA.

We claim:

1. A compound of the formula

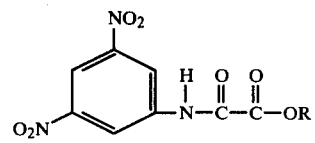

wherein R is alkyl of one to eight carbon atoms, inclusive.

2. A compound in accordance with claim 1 wherein R has two to four carbon atoms, inclusive.

3. A compound in accordance with claim 2 wherein R is ethyl.

4. A compound in accordance with claim 2 wherein R is n-propyl.

5. A compound in accordance with claim 2 wherein R is n-butyl.

6. A pharmaceutical composition which comprises an anti-allergy effective quantity of a compound of the formula

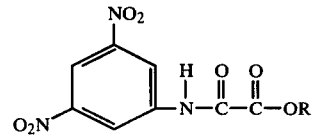

wherein R is alkyl of one to eight carbon atoms, inclusive, in association with a pharmaceutical carrier suitable for oral or parenteral administration.

7. A composition in accordance with claim 6 wherein the carrier is solid.

8. A composition in accordance with claim 6 wherein the carrier is liquid.

9. A composition in accordance with claim 8 wherein the liquid is non-aqueous.

10. A composition in accordance with claim 8 wherein the carrier is aqueous.

11. A composition in accordance with claim 6 wherein the compound is in unit dosage form.

12. A composition in accordance with claim 11 wherein R is alkyl of two to four carbon atoms, inclusive.

13. A composition in accordance with claim 12 wherein R is ethyl.

14. A composition in accordance with claim 6 wherein R is alkyl of two to four carbon atoms, inclusive.

15. A composition in accordance with claim 14 wherein R is ethyl.

16. A method of prophylactically treating allergy of a reagin mediated nature in a mammal which comprises administering to the mammal an anti-allergy effective amount of a compound of the formula

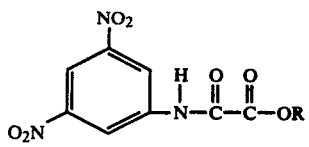

wherein R is alkyl of one to eight carbon atoms, inclusive, in association with a pharmaceutical carrier suitable for oral or parenteral administration.

17. A method in accordance with claim 16 wherein the carrier is solid.

18. A method in accordance with claim 16 wherein the carrier is liquid.

19. A method in accordance with claim 18 wherein the liquid is non-aqueous.

20. A method in accordance with claim 18 wherein the carrier is aqueous.

21. A method in accordance with claim 16 wherein the compound is in unit dosage form.

22. A method in accordance with claim 21 wherein R is alkyl of two to four carbon atoms, inclusive.

23. A method in accordance with claim 22 wherein R is ethyl.

24. A method in accordance with claim 16 wherein R is alkyl of two to four carbon atoms, inclusive.

25. A method in accordance with claim 24 wherein R is ethyl.

UNITED STATES PATENT AND TRADEMARK OFFICE
CERTIFICATE OF CORRECTION

PATENT NO. : 4,172,147
DATED : October 23, 1979
INVENTOR(S) : Charles M. Hall; John B. Wright It is certified that error appears in the above—identified patent and that said Letters Patent is hereby corrected as shown below:

Column 6, line 49, delete the words "or parenteral".

Column 7, line 6, at the beginning of the line insert the word -- orally --.

Column 7, line 19, delete the words "or parental".

Signed and Sealed this

Fifteenth Day of June 1982

[SEAL]

Attest:

GERALD J. MOSSINGHOFF

Attesting Officer    Commissioner of Patents and Trademarks